(12) United States Patent
Kislinger et al.

(10) Patent No.: US 10,368,742 B2
(45) Date of Patent: Aug. 6, 2019

(54) OPHTHALMIC SYSTEM

(71) Applicant: Eyenez, LLC, Glendora, CA (US)

(72) Inventors: Mark B. Kislinger, Glendora, CA (US); Emerick S. Varga, Pasadena, CA (US)

(73) Assignee: Eyenez, LLC, Glendora, CA (US)

( * ) Notice: Subject to any disclaimer, the term of this patent is extended or adjusted under 35 U.S.C. 154(b) by 0 days.

(21) Appl. No.: 15/856,578

(22) Filed: Dec. 28, 2017

(65) Prior Publication Data

US 2018/0132715 A1 May 17, 2018

Related U.S. Application Data

(63) Continuation-in-part of application No. 15/487,781, filed on Apr. 14, 2017.

(60) Provisional application No. 62/533,779, filed on Jul. 18, 2017, provisional application No. 62/322,421, filed on Apr. 14, 2016.

(51) Int. Cl.
*A61B 3/14* (2006.01)
*A61B 3/00* (2006.01)
*A61B 3/15* (2006.01)

(52) U.S. Cl.
CPC .............. *A61B 3/14* (2013.01); *A61B 3/0008* (2013.01); *A61B 3/15* (2013.01)

(58) Field of Classification Search
CPC ........... A61B 3/14; A61B 3/0025; A61B 3/12; A61B 3/102; A61B 3/0058
USPC ........................................................ 351/206
See application file for complete search history.

(56) References Cited

U.S. PATENT DOCUMENTS

| | | | |
|---|---|---|---|
| 4,200,362 A | 4/1980 | Pomerantzeff | |
| 6,299,307 B1 | 10/2001 | Oltean et al. | |
| 8,356,898 B2 * | 1/2013 | Ono | A61B 3/14 351/206 |
| 8,836,778 B2 * | 9/2014 | Ignatovich | A61B 3/1208 348/77 |
| 8,911,088 B2 * | 12/2014 | Van Saarloos | A61B 3/14 351/206 |
| 2005/0270484 A1 * | 12/2005 | Maeda | A61B 3/185 351/206 |
| 2008/0259274 A1 * | 10/2008 | Chinnock | A61B 3/14 351/206 |
| 2012/0050515 A1 * | 3/2012 | Shikaumi | A61B 3/0008 348/78 |
| 2013/0077047 A1 * | 3/2013 | Uchida | A61B 3/12 351/206 |
| 2016/0066783 A1 | 3/2016 | Kislinger et al. | |

* cited by examiner

Primary Examiner — Mohammed A Hasan
(74) Attorney, Agent, or Firm — Fishman Stewart PLLC

(57) ABSTRACT

An ophthalmic system and method for imaging an eye includes an eye guard, an objective lens, such that light passes through the objective lens along an illumination path that passes through the eye guard, a light source positioned to emit imaging light along the illumination path, a camera assembly positioned to receive emitted light that is emitted from a back surface of the eye. The light source and the objective lens are positioned such that, when the eye guard is positioned proximate the eye of the patient, the imaging light passes through a first portion of a pupil opening in the eye, and the emitted light passes through a second portion of the pupil opening of the eye that is different from the first portion, and wherein the camera assembly captures an image of the eye using the emitted light.

20 Claims, 18 Drawing Sheets

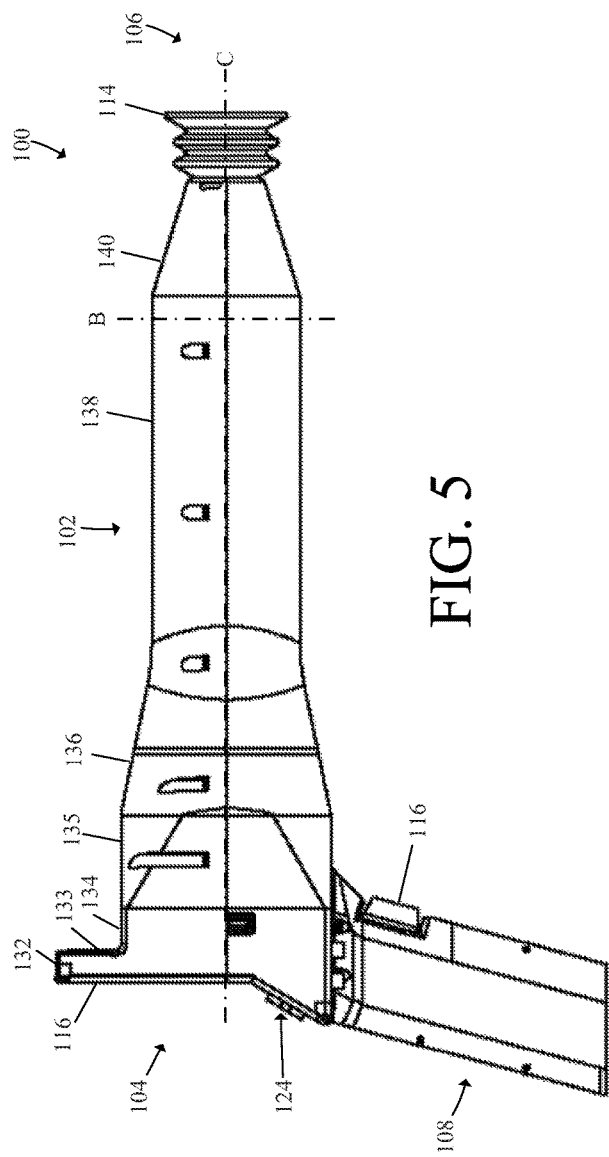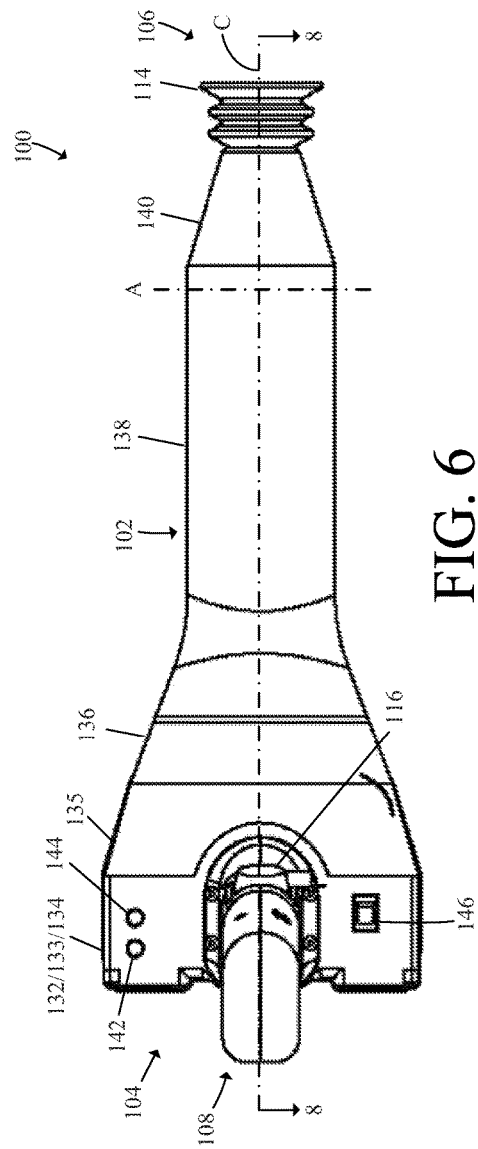

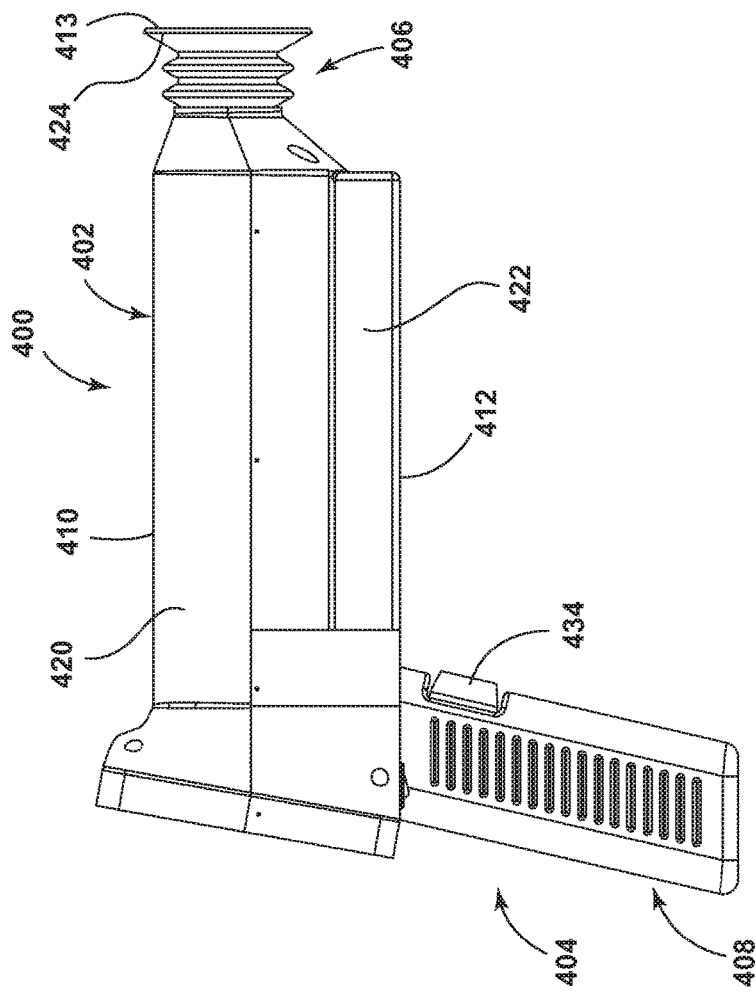
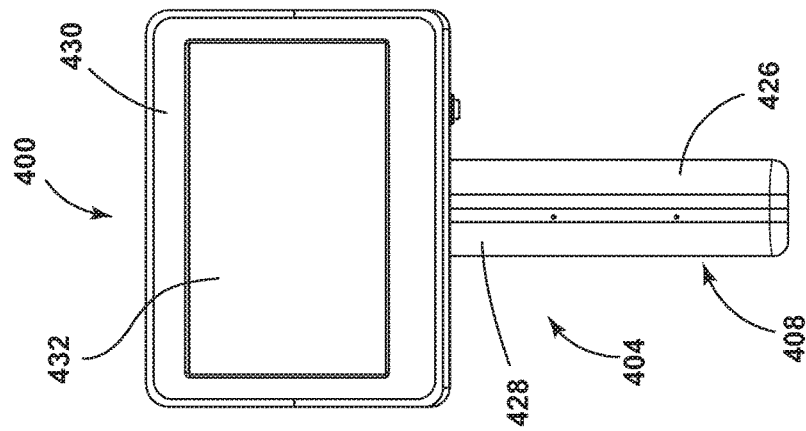
FIG. 15B
FIG. 15A

OPHTHALMIC SYSTEM

CROSS REFERENCE TO RELATED APPLICATIONS

This application is based on and claims priority to U.S. Provisional Patent Application No. 62/533,779, filed Jul. 18, 2017, and is a continuation-in-part of and claims priority to U.S. Non-Provisional patent application Ser. No. 15/487,781, filed Apr. 14, 2017, which claims priority to U.S. Provisional Patent Application No. 62/322,421, filed Apr. 14, 2016, all of which are hereby incorporated by reference in their entirety.

BACKGROUND

Traditional cameras for obtaining images of an eye utilize a multi-angle imaging path with numerous reflecting surfaces. Each reflecting surface and bend in the imaging path results in loss of light transmission, thereby distorting the image captured by the camera. Further, light sources utilized by these traditional cameras may be insufficient to capture a diagnostic image of the eye without using medication to dilate the eye. Traditional devices further lack enhanced autofocus and image filtering capabilities. Some known systems include imaging of an eye, but can include reflections off of an objective lens and/or reflections off of the cornea, which can lead to blurring in the image or can interfere with a proper capture of an image.

There is a need for an improved system with an inline configuration that reduces or is substantially free of reflecting surfaces and bends in the imaging path to minimize distortion of the image. This system may be configured to minimize constriction of the eye to capture of a diagnostic image of an eye in a partially or fully dilated condition without using medication to dilate the eye. This system may also include enhanced lighting, autofocus, and image filtering capabilities. Thus, this improved system may provide for enhanced detection of eye disorders as well as early detection of other bodily disorders that have complications resulting in eye disorders.

BRIEF DESCRIPTION OF THE DRAWINGS

FIG. 5 illustrates a side view of the exemplary system;
FIG. 6 illustrates a bottom view of the exemplary system;
FIG. 15A illustrates a front view of the illustration in FIG. 14;
FIG. 15B illustrates a side view of the illustration in FIG. 14.

DETAILED DESCRIPTION

An ophthalmic system may be configured to provide enhanced imaging an eye of a patient. The system may include a housing, a lens, and a control assembly. The housing may extend along a central axis and between a proximal portion and a distal portion. The housing may include upper and lower housing portions and a handle. The lens may include a lens axis and may be disposed in the distal portion of the housing. The control assembly may be disposed in the proximal portion of the housing. The control assembly may include and may operatively connect a control panel, a camera assembly having a camera axis, and a lighting assembly. The lighting assembly may include a non-visible light source configured to focus the camera assembly and a visible light source configured to capture an image of the eye. The lens axis and the camera axis may be along the central axis of the housing, thereby forming an inline configuration that reduces or is substantially free of reflecting surfaces and bends in the imaging path to minimize distortion of the image.

Methods of using an ophthalmic system for imaging an eye of a patient are also contemplated. A method may include providing the lens, the camera assembly, the lighting assembly, the control panel, the trigger, and the display. The method may further comprise positioning the camera assembly toward the eye, activating, by way of the control panel, the non-visible light source, displaying, by way of the display, the eye with the camera assembly, focusing, by way of the control panel, the camera assembly under light from the non-visible light source, activating, by way of the trigger, the visible light source after deactivating the non-visible light source, capturing, after a predefined delay, the image of the eye under light from the visible light source, re-activating the non-visible light source after capturing the image, and re-displaying, by way of display, the eye with the camera assembly under light from the non-visible light source.

Figure 1:
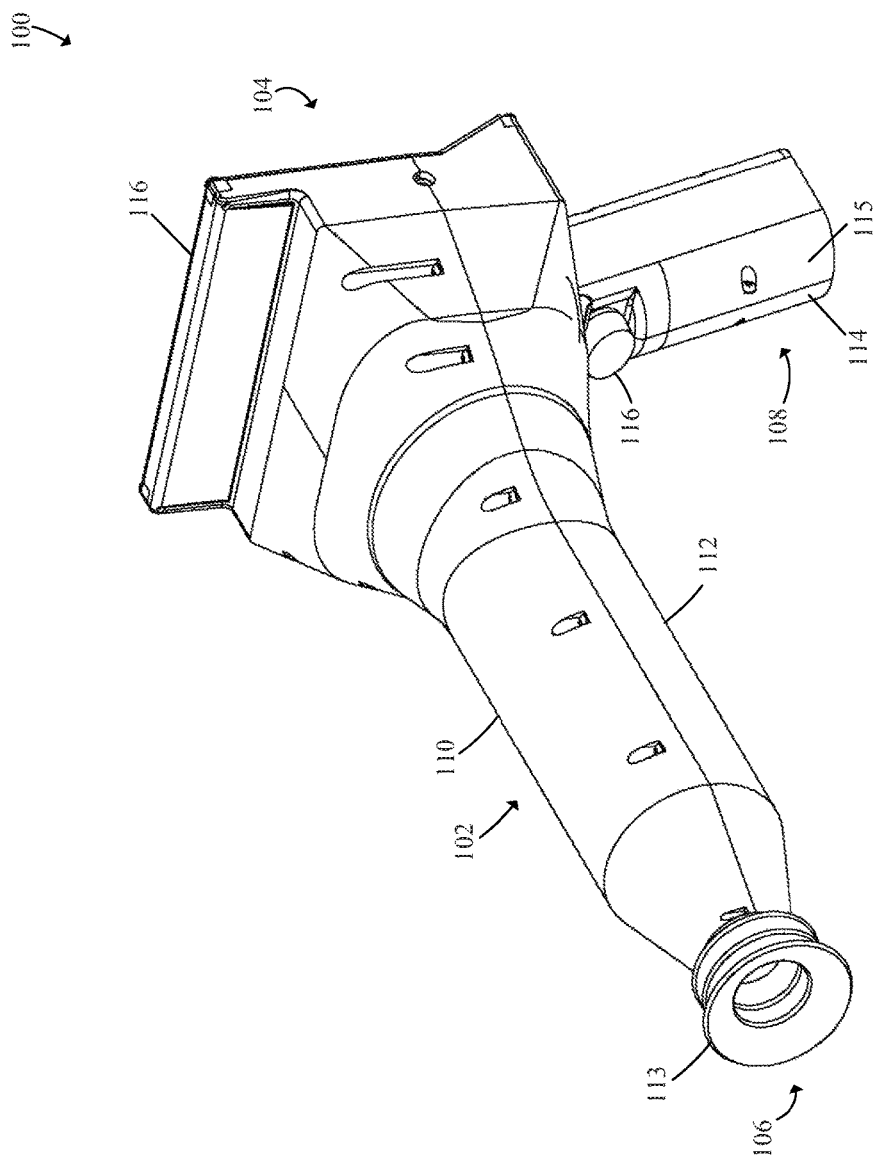
FIG. 1 illustrates an isometric, front view of an exemplary system of the present disclosure.

FIG. 1 illustrates an exemplary system 100, for example, an ophthalmic system configured to identify eye disorders. System 100 may take many different forms and include multiple and/or alternate components and facilities. While an exemplary system 100 is shown in FIG. 1, the exemplary components illustrated in FIG. 1 are not intended to be limiting. Indeed, additional or alternative components and/or implementations may be used.

The system 100 may be configured to facilitate examination of an eye, for example, to identify, image or photograph, and diagnose an eye disorder by viewing inner structures of the eye including, for example, the retina, optic disc, macula, and posterior pole, also called the fundus. By providing a view of the inner structures of the eye, the system 100 may be utilized to diagnose eye disorders.

In an exemplary use, the system 100 may be configured to identify an eye disorder, for example, during an eye examination by an examiner or user such as an ophthalmologist, optometrist, optician, eye technician, or any other medical professional. An eye disorder may include, for example, any disorder that is viewable from the inner structures of the eye. Exemplary eye disorders may include any disorder affecting the normal function of the eye, for example, an eye disease, damage to the eye (e.g., resulting from trauma or another bodily disease), or any other vision disorder. Exemplary eye disorders may include, without limitation, diabetic retinopathy, age-related macular degeneration (AMD), allergies, amblyopia (also referred to as "lazy eye"), astigmatism, bacterial keratitis, cataracts, conjunctivitis (also referred to as "pink eye"), detached and torn retina, dry eye, floaters and flashes, glaucoma, low vision, and presbyopia (also referred to as "aging eye"). Accordingly, the system 100 may be utilized to identify and diagnose any condition affecting normal function of the eye.

Furthermore, the system 100 may be configured to identify other bodily disorders, for example, during a physical examination by a user such as general medical practitioner or any other medical professional. The system may be configured to detect complications viewable from the inner structures of the eye. For example, the system 100 may be utilized to identify diabetic retinopathy of the eye resulting from diabetes. The system 100 may be utilized to identify hypertension, glaucoma, papilledema, and any other bodily disorder affecting the eye.

As shown in FIG. 1, an exemplary system 100 may include a housing 102. The system 100 may include a proximal portion 104 configured for operation by a user and a distal portion 106 configured to be positioned toward and engage an eye socket about an eye of a patient. In one example, the patient may be a human patient, however, it is contemplated that the disclosure may be applicable to non-human patients, such as animals to include pets and the like. The housing 102 may include an upper housing portion 110 and a lower housing portion 112, e.g., with the upper housing portion 110 having a lower periphery that engages an upper periphery of the lower housing portion 112.

The housing 102 may include a handle 108, e.g., extending from the lower housing portion 112. The proximal portion 104, the distal portion 106, and the handle 108 may be configured for examination of an eye of a patient by a user. The proximal portion 104 may be configured to be positioned near the user during examination and through which the user examines the eye while holding the handle 106. The distal portion 106 may be configured to be positioned toward the eye during examination. The handle 108 may include first and second handle portions 114, 115, e.g., with the first handle portion 114 having a first periphery that engages a second periphery of the second handle portion 115 in an opposing arrangement. The system 100 may include an engagement member 113 on the distal side 106 of the housing 102, e.g., having an accordion shape. The engagement member 113 may include a proximal portion configured to engage the housing 102 and a distal portion configured to flexibly conform to an eye socket of the patient. A trigger 116 may be slidably or rotatably received by the handle 108 and in operative communication with a camera. The trigger 116 may be configured to initiate capture of an image through the engagement member 113, e.g., in response to an inward force by the user and toward the handle 108. The system 100 may be configured to automatically or manually focus and display structures of the eye at multiple depths.

Figure 2:
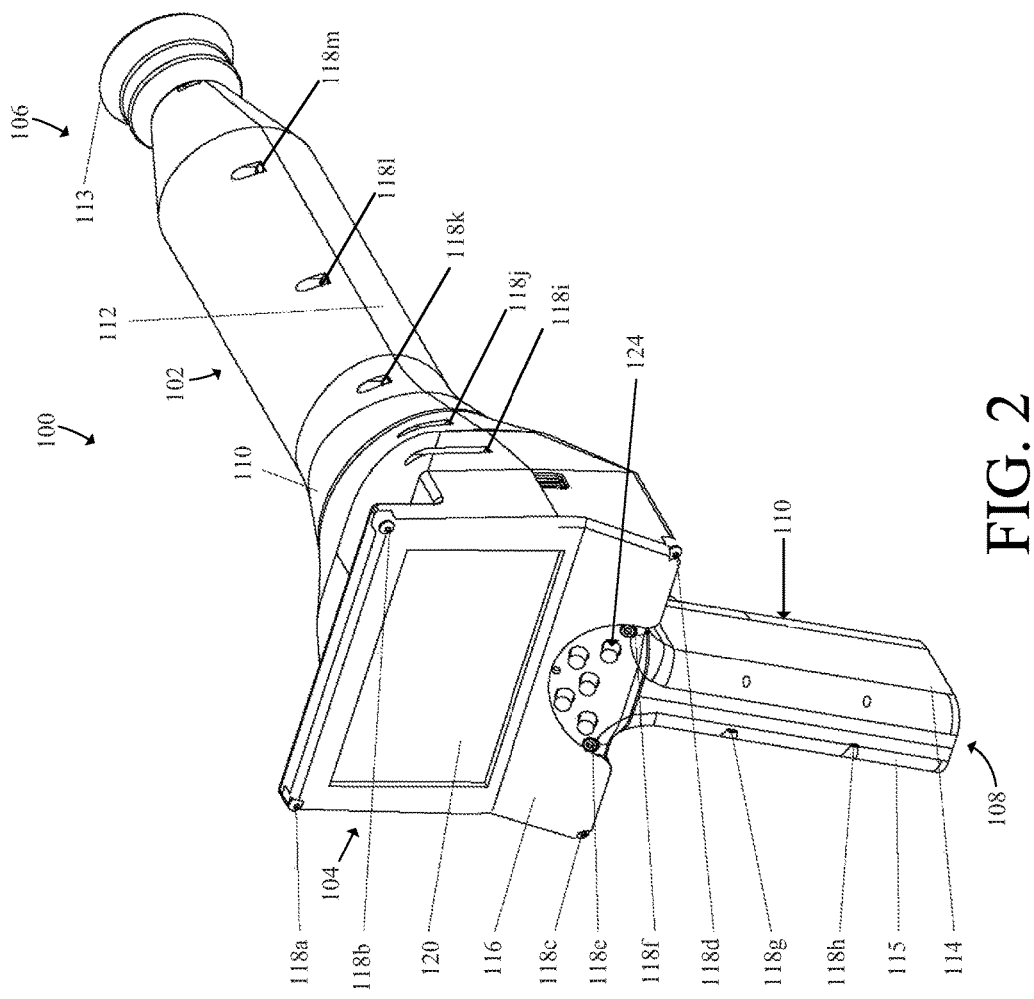
FIG. 2 illustrates an isometric, back view of the exemplary system.

As shown in FIG. 2, the system 100 may further include a plurality of fasteners 118, a display 120, a display housing 116, and a control panel 124. The display 120 may be configured to display images of an eye of a patient. The display housing 116 may include an upper portion with a window configured to engage an outer perimeter of the display 120 and secure the display 120 relative to the housing 102. The display housing 120 may include a lower portion angled with respect to the upper portion of the display housing 120 and configured to secure the control panel 124 relative to the housing 102 and adjacent the handle 108.

The plurality of fasteners 118 may be configured to secure the portions of the housing 102 relative to each other. Fasteners 118a, 118b may be configured to secure first and second upper corners of the display housing 120 relative to the housing 102, e.g., an upper, proximal portion of the upper housing 110. Fasteners 118c, 118d may be configured to secure first and second lower corners of the display housing 120 relative to the housing 102, e.g., a lower, proximal portion of the lower housing 112. Fasteners 118e, 118f may be configured to secure the control panel 124 relative to the housing 102, e.g., a lower, proximal portion of the lower housing 112. Fasteners 118g, 118h may be configured to secure the first periphery of the first handle portion 114 against the second periphery of the second handle portion 115, thereby securing the first and second handle portions 114, 115 together. Fasteners 118i-m may be configured to secure the lower periphery of the upper housing 110 relative to the upper periphery of the lower housing 112.

Figure 3:
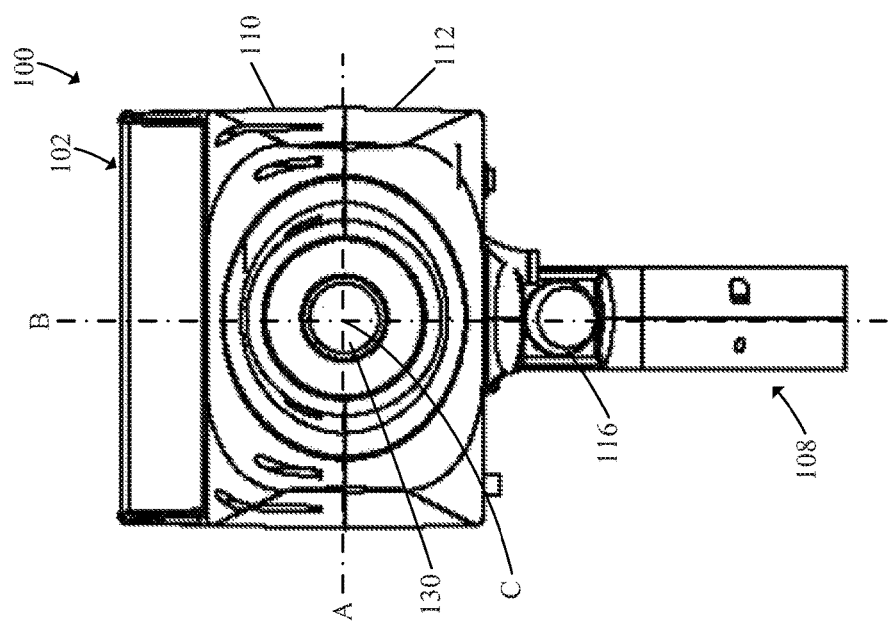
FIG. 3 illustrates a front view of the exemplary system.

Referring to FIG. 3, the system 100 may include a lens 130. The lens 130 may be horizontally positioned with respect to the housing 102 along an axis A, e.g., along the lower periphery of the upper housing portion 110 and the upper periphery of the lower housing portion 112. The lens 130 may be vertically positioned with respect to the housing along an axis B, e.g., along the first periphery of the first handle portion 114 and the second periphery of the second handle portion 115. The lens 130 may be axially positioned at a distal portion of the housing 102 along an axis C, e.g., through the intersection of axes A and B.

Figure 4:
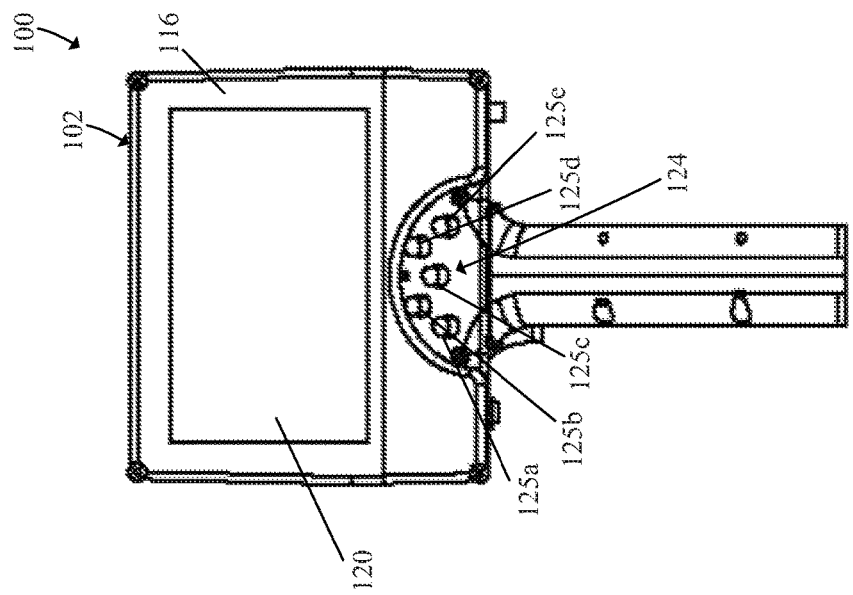
FIG. 4 illustrates a back view of the exemplary system.

As shown in FIG. 4, the control panel 124 may include a plurality of buttons 125a-e. The control panel 124 may be operatively connected to a lighting assembly and a camera lens assembly, as discussed in further detail below. Buttons 125a and 125b may be configured to respectively decrease and increase light intensity of the lighting assembly. Button 125c may be configured to change a mode of various modes including a settings mode, an image viewing mode, an image capture mode, and an image transmit mode. Buttons 125d, 125e may be configured to respectively focus out and focus in the camera assembly.

Referring to FIGS. 5-6, the housing 102 may include various structures that are optimized to engage internal components while facilitating examination of an eye. Housing 102 may include an outer surface that varies in structure from the proximal portion 104 to the distal portion 106 of the system 100 as shown in FIGS. 5-6. The housing 102 may further include an inner surface separated by a thickness from the outer surface and with the surfaces of the outer surface, but with internal features to engage and secure the internal components. The housing 102 may include a first proximal portion 132, a second proximal portion 133, a third proximal portion 134, a first intermediate portion 135, a second intermediate portion 136, a third intermediate portion 138, and a distal portion 140. The first proximal portion 132 may include a rectangular cross section relative to axis C and may be configured to engage the display housing 116 and to receive the display 120. The second proximal portion 133 may extend from the first proximal portion 132 and inwardly toward along axis B as shown in FIG. 5 and along axis C as shown in FIG. 6. The third proximal portion 134 may extend from the housing portion 133 along the axis C with a rectangular cross section as shown by FIGS. 5 and 6. The first intermediate portion 135 may extend from the third proximal portion 134 along axis C as shown in FIG. 5 and taper inwardly relative to axis A as shown in FIG. 6. The second intermediate portion 136 may extend from the first intermediate portion 135 and taper inwardly relative to axes B and A as shown in FIGS. 5 and 6, respectively. The third intermediate portion 138 may extend from the second intermediate portion 136 with a circular or oval cross section and along axis C as shown in FIGS. 5 and 6. The distal portion 140 may extend from the third intermediate portion 138 and taper inwardly along axes B and A as shown in FIGS. 5 and 6, respectively. The handle assembly 108 may extend at an angle from a lower portion of the housing 102 and may include the trigger 116 as shown in FIGS. 5 and 6. The housing 102, e.g., a lower portion, may include buttons 142, 144, 146 that may be configured as respective menu up, menu down, and power buttons.

Figure 7:
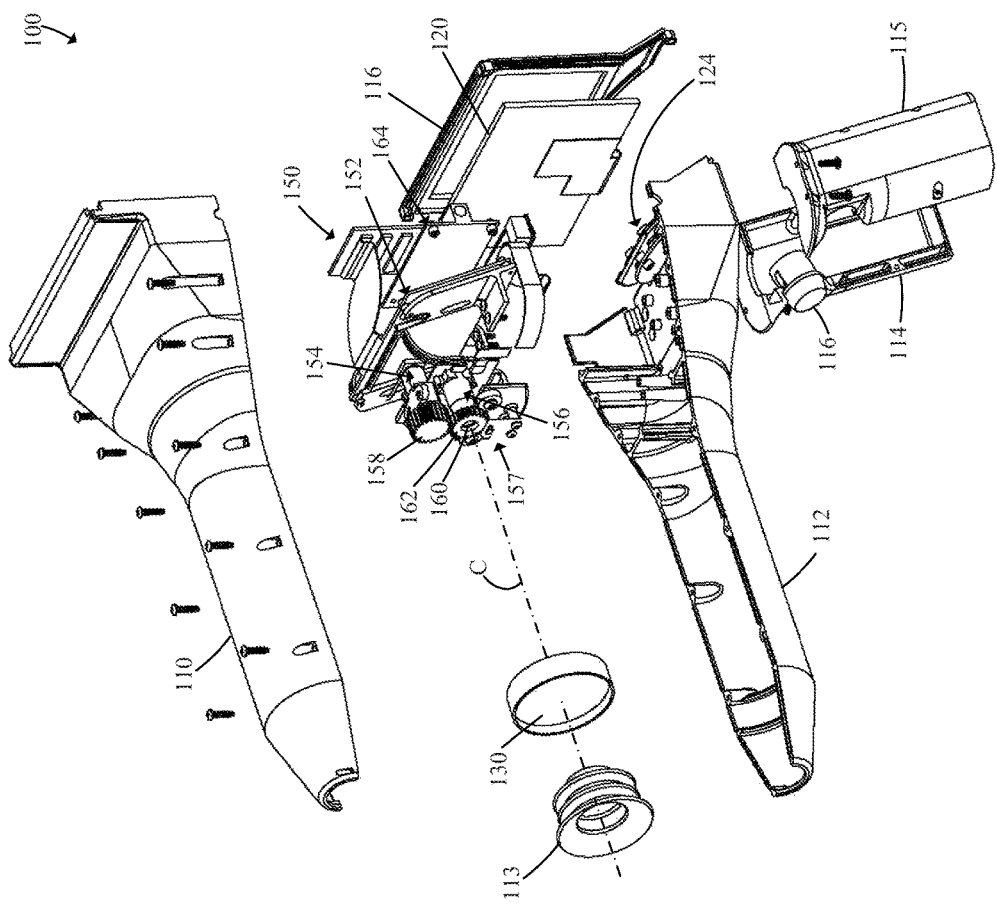
FIG. 7 illustrates an exploded view of FIG. 1.
Figure 8:
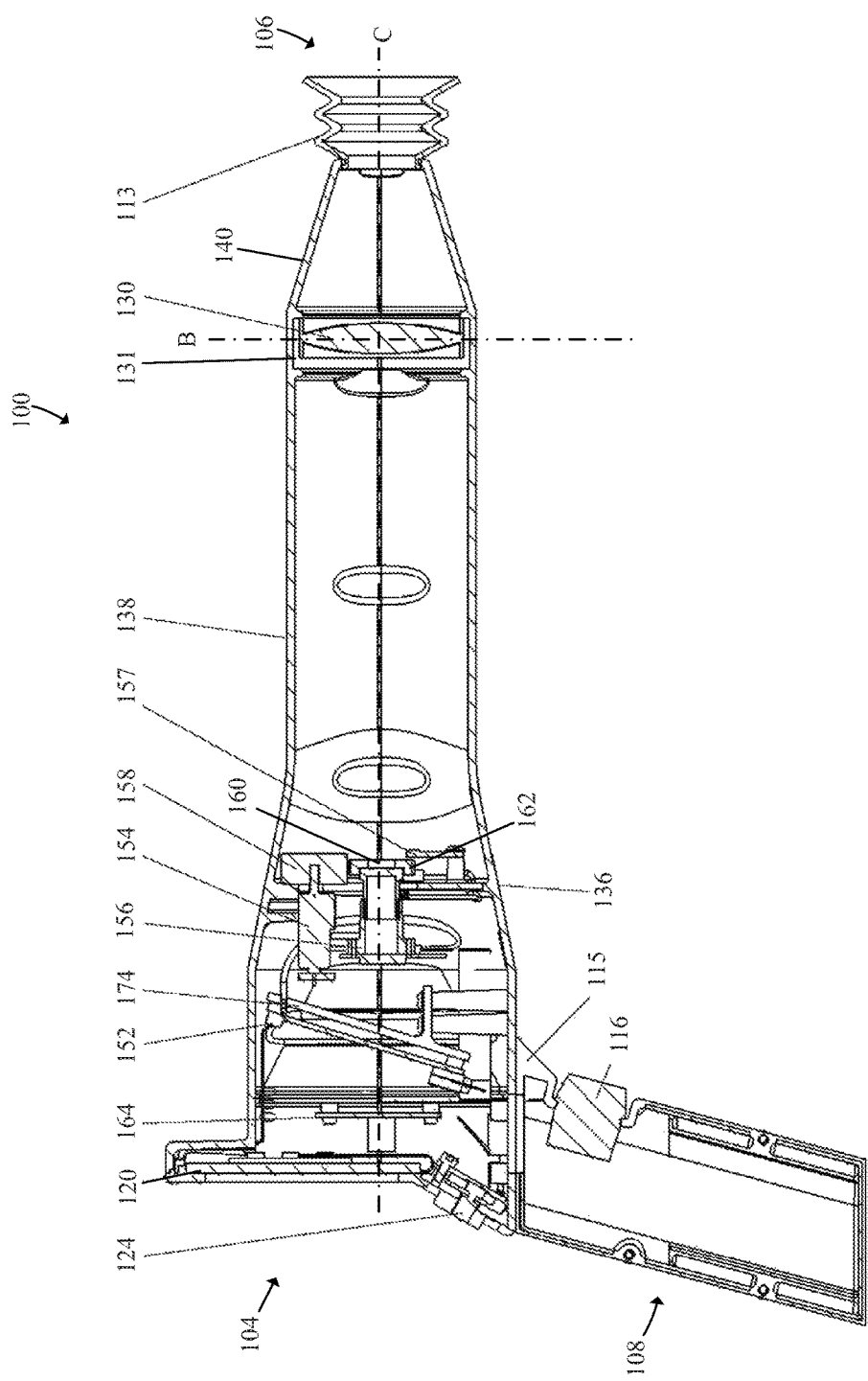
FIG. 8 illustrates a cross section view of FIG. 5.
Figure 9:
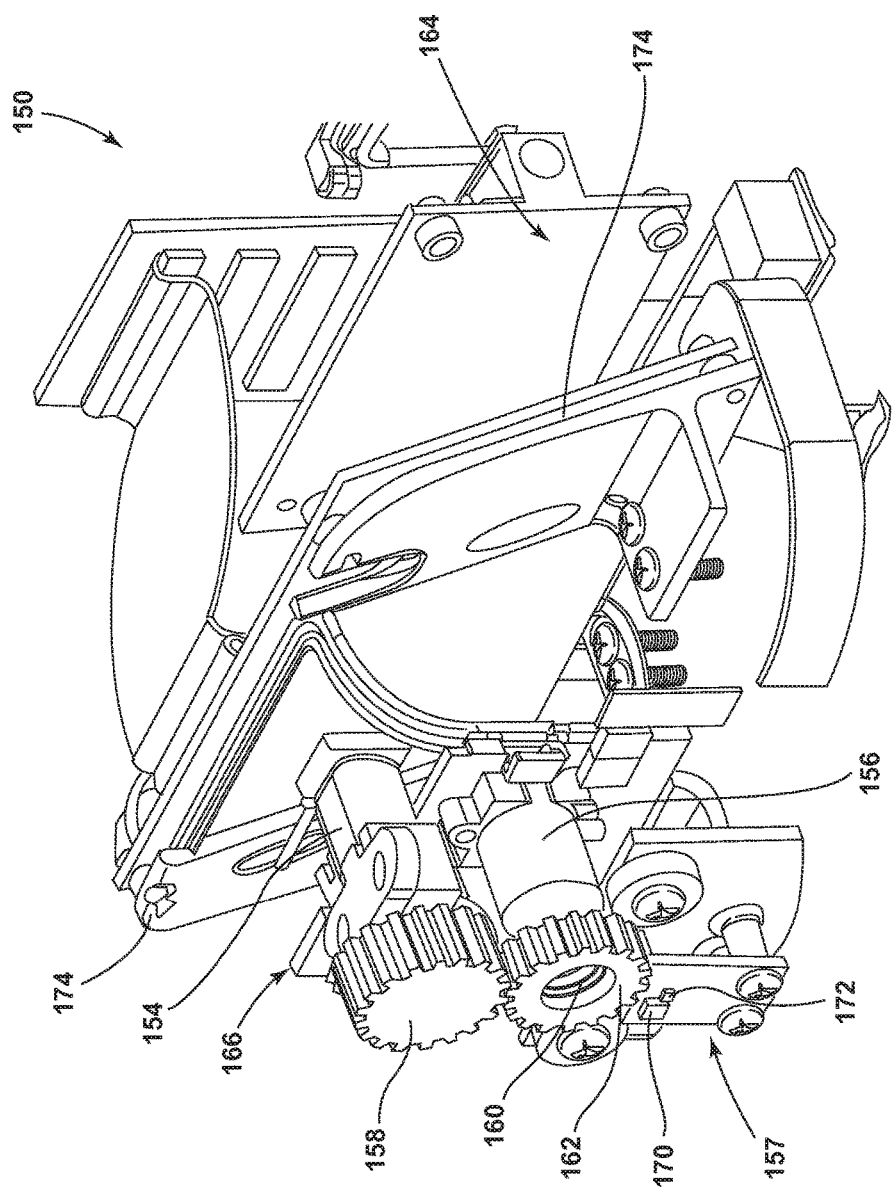
FIG. 9 illustrates an isometric view of a control assembly of the exemplary system.

With reference to FIGS. 7-9, the system 100 may further include a control assembly 150. As shown in FIG. 7, the control assembly 150 may include the control panel 124, an electronic based control board 152 (e.g., one or more printed circuit boards (PCBs)), an actuator 154, a camera assembly 156, and a lighting assembly 157. The control board 152 may operatively connect and power the control panel 124, the actuator 154, the camera assembly 156, and the lighting assembly 157. The control board 152 may further include an encoder configured to translate an input from the control panel 124 into an output that moves the actuator 154.

As shown in FIGS. 7 and 8, the system 100 may include an inline arrangement with a linear optical path, e.g., between the lens assembly 130 and the camera assembly 156 for the eye image returning from the eye. A central axis of the optical assembly 160 of the camera assembly 156 and a central axis of the lens assembly 130 may be aligned with axis C. This may provide a linear path along axis C for light to pass to and/or from the eye of the patient. As such, the lens axis and the camera axis form an inline configuration, which may also be aligned with a central axis of the housing. Thus, the camera assembly and the lens are arranged in an optical path for the eye image that is, e.g., linear and substantially free of bends and reflective surfaces, e.g., mirrored surfaces. To increase image quality, this linear path along axis C provides a direct path to the eye that is unobstructed by and substantially free of reflective surfaces from the lens assembly 130 to the camera assembly 156.

The control board 152 may be configured to selectively control one or more light sources, as described in further detail below. The control board 152 may be configured to automatically or manually adjust an amount of power provided to one or more light sources. An exemplary control board 152 may include or may be operatively connected to an adjustable voltage divider, e.g., an analog or digital potentiometer with a sliding or rotating contact. The control board 152 may be configured to control a light intensity or brightness of the one or more light sources, for example, to adjust the amount of light used in conjunction with the image captured by the camera assembly 156. The control board 152 may be selectively adjusted to provide a lower or an intermediate light intensity, for example, to promote full dilation of the eye or may be selectively adjusted to provide a full light intensity, for example, to promote capture of an image by the camera assembly 156.

Referring to FIG. 9, the control board 156 may receive one or more inputs from the control panel 124 and, in response, cause the actuator 154 to move rotationally or linearly. The actuator 154 may include a first drive member 158, e.g., a gear having a plurality of teeth about its outer circumference. The camera assembly 156 may include an optical assembly 160 and a second drive member 162, e.g., a gear with having a plurality of teeth about its outer circumference. The respective teeth of the actuator 154 and the camera assembly 156 may be configured to interdigitate, thereby translating rotation of the first drive member 158 to the second drive member 162.

The optical assembly 160 may include one or more camera lenses having relative distances that are retracted or expanded in response to one or more inputs from the control panel 124, e.g., to zoom in and out the image presented on the display 120. For example, the optimal assembly 160 may be configured to retract or expand the one or more camera lenses in response to rotation of a second drive member 162. As such, in response to one or more inputs from the control panel 124, the control panel 124 may cause the control board 156 to move the first drive member 158, thereby rotating the second drive member 162. Rotation of the second drive member 162 may cause the one or more lenses to retract or expand, thereby providing focus adjustment for the image on the display 120.

As shown in FIG. 9, the control assembly 150 may further include a sensor assembly 166. The sensor assembly 166 may include a processor, a memory, and one or more sensors that are operatively connected to capture images of internal structures of an eye, e.g., through the camera assembly 160, lens 130, and engagement member 113. The one or more sensors may be configured to detect light or electromagnetic energy. An exemplary sensor may include a photocell, photo resistor, photodiode, reverse-biased LED, or charge-coupled device. The sensor may be configured to detect light emitted to and reflected from an eye of a patient, e.g., to be stored to the memory and presented on the display 120.

The system 100 may further be configured for image processing and distribution. The system may include autofocus to automatically focus or manual focus to manually focus the camera assembly 160 relative to the internal structures of the eye (e.g., using a processor), capture an image of the eye (e.g., using the sensor), store the image of the eye (e.g., as part of the memory), and transfer the image (e.g., using a wired connection with a data cable or a wireless connection with the transceiver) to one or a plurality of other computing devices.

Referring again to FIG. 9, the lighting assembly 157 may include one or more light sources 170, 172 configured to illuminate the eye, e.g., for capture of an image. Exemplary light source 170 may include a light source that primarily emits visible light such as a light emitting diode (LED), a halogen light source, or an incandescent light source. Exemplary light 172 may include a light source that primarily emits non-visible light such as an infrared (IR) light source. The control assembly 150 may be operatively connected with the lighting assembly 157 to emit light in conjunction with the capture of the image by the sensor assembly 166, e.g., the sensor assembly 166 capturing the image after a predefined delay. The light sources 170, 172 may include a lighting axis that is offset from the central axis C or along the central axis C, e.g., with the non-visible 172 and visible 170 light sources arranged in a circular array about the central axis C. The light sources 170, 172 may be configured to operate in conjunction with each other. The light sources 170, 172 may be configured to emit light at for a predefined or user-defined duration and intensity. For example, the light source 172 may include an IR light source 128 to allow a user to focus the camera assembly 160 on the eye and, in response to the trigger 116 being pulled, the light source 170 may be used to illuminate the eye with visible light for capture of an image by the camera assembly 160.

The display 120 may be configured to present one or more images from the sensor assembly 166. The display 120 may be communicatively connected with the control assembly 150. The display 120 may be configured to receive images from the control assembly 150. The display 120 may be configured to present one or more images of the eye captured by the camera. The display may include a touchscreen configured to receive inputs in response to being touched by the user.

The system 100 may further include a power control assembly 164. The power control assembly 164 may be operatively connected to a power source that is configured to provide power to power system 100. The power source may be positioned anywhere in the system 100, e.g., in the handle 108. An exemplary power source may include a DC power source, an AC power source, or a combination thereof. An exemplary DC power source may include a battery, for example a lithium-ion, nickel-cadmium, alkaline, lithium, nickel oxyhydroxide, or silver-oxide battery. The power source 228 may be rechargeable or non-rechargeable.

Figure 10:
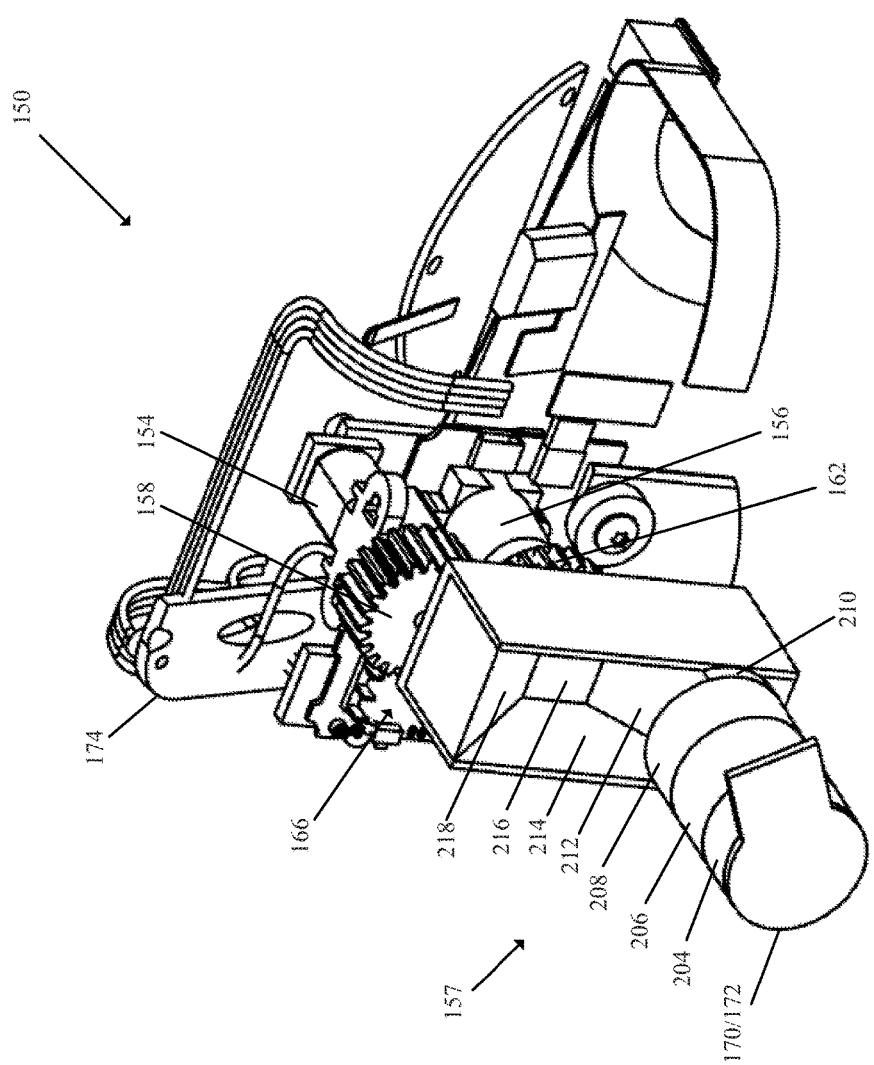
FIG. 10 illustrates an alternative control assembly.
Figure 11:
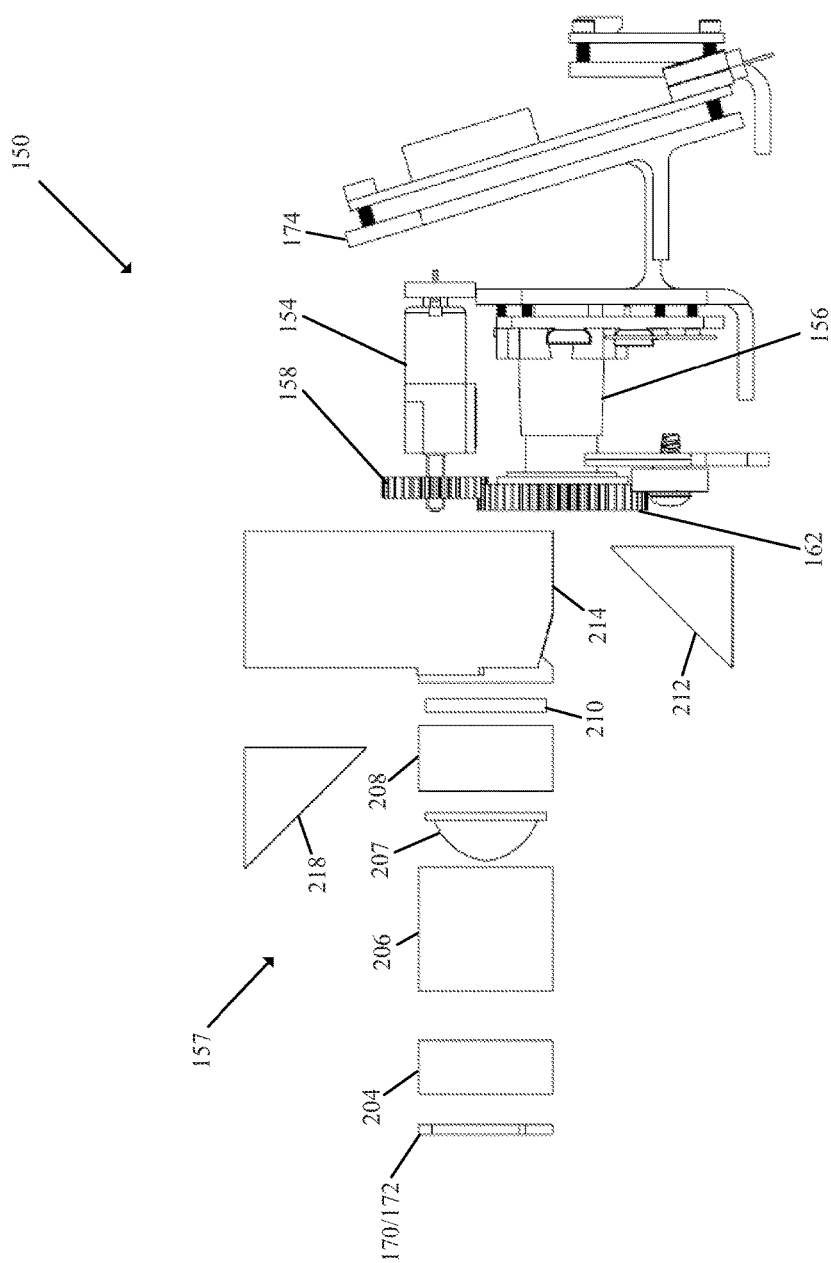
FIG. 11 illustrates an exploded view of FIG. 10.
Figure 12:
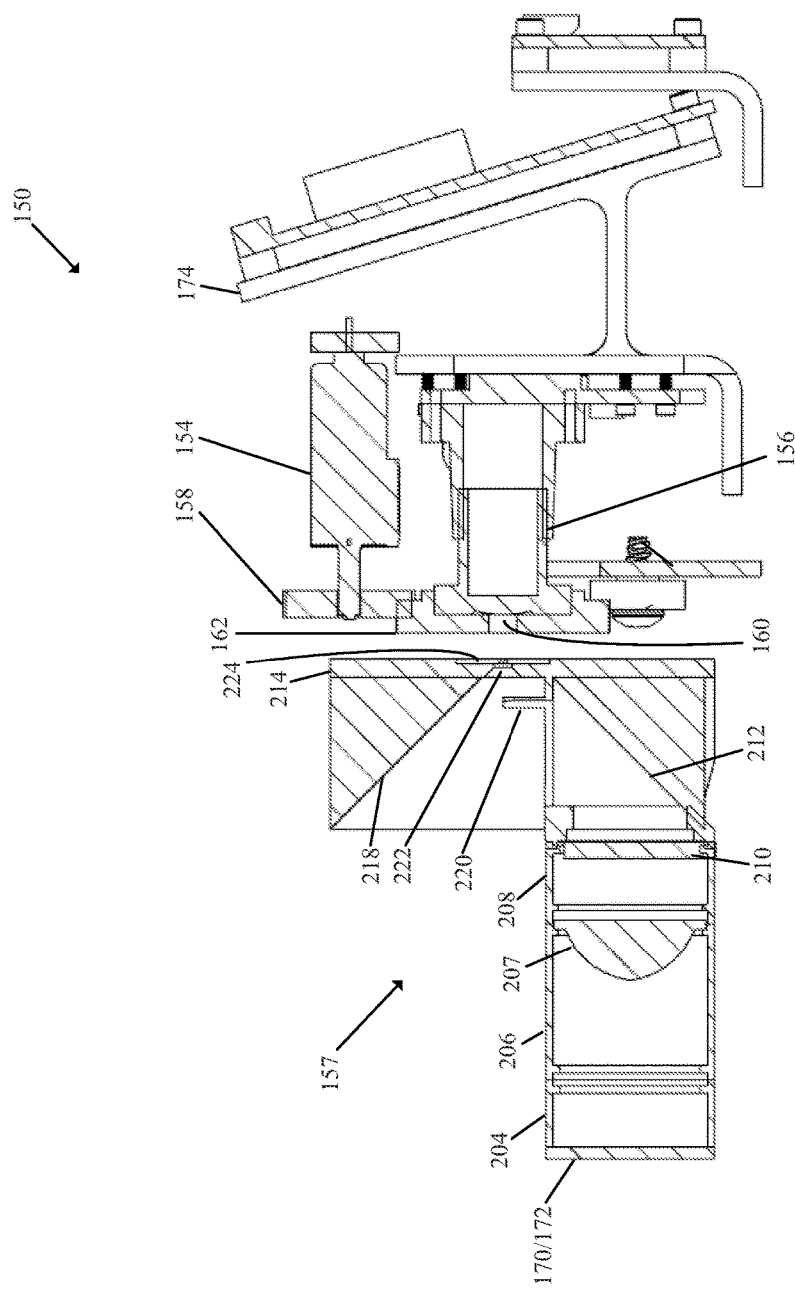
FIG. 12 illustrates a cross section view of FIG. 10.

Referring to FIGS. 10-12, lighting assembly 157 may include further configurations to optimize lighting, e.g., while utilizing a linear optical path between the optical assembly 160 and the lens assembly 130. Lighting assembly 157 may include one or both of light sources 170/172, e.g., in a circular or alternating arrangement. As shown in FIG. 10, lighting assembly 157 may further include a diffusor housing 204 to evenly distribute light emitted from light sources 170/172, a lens housing 206 to channel light from diffusor housing 204 to a condensing lens 207 as described below, a polarizer housing 208 to channel light from the condenser lens 207 to a linear polarizer 210 to reduce glare by eliminating light that is polarized in one direction, mirrors 212/218 including right angle mirrors to redirect light approximately 90 degrees, and a mirror housing 214 including a first side surface, a second side surface, and an aperture surface 216. The mirror housing 214 may be configured to position mirrors 212/218 relative to the surrounding components and direct light to optical assembly 160. As shown FIG. 11, lighting assembly 157 may further include condensing lens 207 to collimate light from diffusor housing 204 and pass the collimated light to polarizer housing 208. As shown in FIG. 12, lighting assembly 157 may further include a protrusion 220 extending from mirror housing 214 and to minimize stray light from entering optical assembly 160, an aperture 222 having a conical reflector and a passage aligned with optical assembly 160, and a linear polarizer 224 to reduce glare by eliminating light that is polarized in one direction. System 100 may be configured to polarize light and reduce glare from the lens assembly 130, lighting assembly 157, camera assembly 156, light sources 170/172, or any combination thereof.

Methods may include using the system 100 for imaging an eye of a patient. A method may include providing the lens 130, the camera assembly 156, the lighting assembly 157, the control panel 124, the trigger 116, and the display 120. The method may further comprise positioning the camera assembly 156 toward the eye, activating, by way of the control panel 124, the non-visible light source 172, displaying, by way of the display 120, the eye with the camera assembly 156, focusing, by way of the control panel 124, the camera assembly under light from the non-visible light source 172, activating, by way of the trigger, the visible light source 170 after deactivating the non-visible light source 172, capturing, after a predefined delay, the image of the eye under light from the visible light source 170, re-activating the non-visible light source 172 after capturing the image, and re-displaying, by way of display 120, the eye with the camera assembly 156 under light from the non-visible light source 172.

Thus, an ophthalmic system may be configured to image an eye of a patient. The system may include a housing, a lens, and a control assembly. The housing may extend along a central axis and between a proximal portion and a distal portion. The lens with a lens axis may be disposed in the distal portion of the housing. The control assembly may be disposed in the proximal portion of the housing. The control assembly may include and operatively connect a camera assembly having a camera axis and a lighting assembly. The lighting assembly may include a non-visible light source configured to focus the camera assembly and a visible light source configured to capture an image of the eye. The lens axis and the camera axis may be along the central axis of the housing.

Also disclosed is a method and apparatus for eliminating reflections off of the objective lens and reflections off of the cornea. The disclosed method and apparatus incorporate the features described in FIGS. 1-12 above, and are further described in FIGS. 13-18B. Cross linear polarizers in the disclosed system are used to eliminate reflections off of the objective lens. The polarizers described here and throughout the disclosure refer generally to linear polarizers that polarize light to a given plane along a direction of propagation. For instance, light from an LED or other light source passes through one polarizer to place it into an S orientation, and the light that is reflected off of the objective lens keeps or retains the S orientation, and is then rejected by a polarizer that is placed in a P orientation in front of the camera. The light that goes through the objective and reaches the retina is absorbed and re-emitted in both the P and S orientations, allowing the light that is in the P orientation to pass back to the camera. To eliminate corneal reflections, the illumination path and imaging path are decoupled from one another. One illumination path travels through the top portion of the pupil opening while returning light goes through the bottom half of the pupil opening. This decoupling means that the light reflected off of the cornea from the top half never finds its way back through the imaging path.

Figure 13:
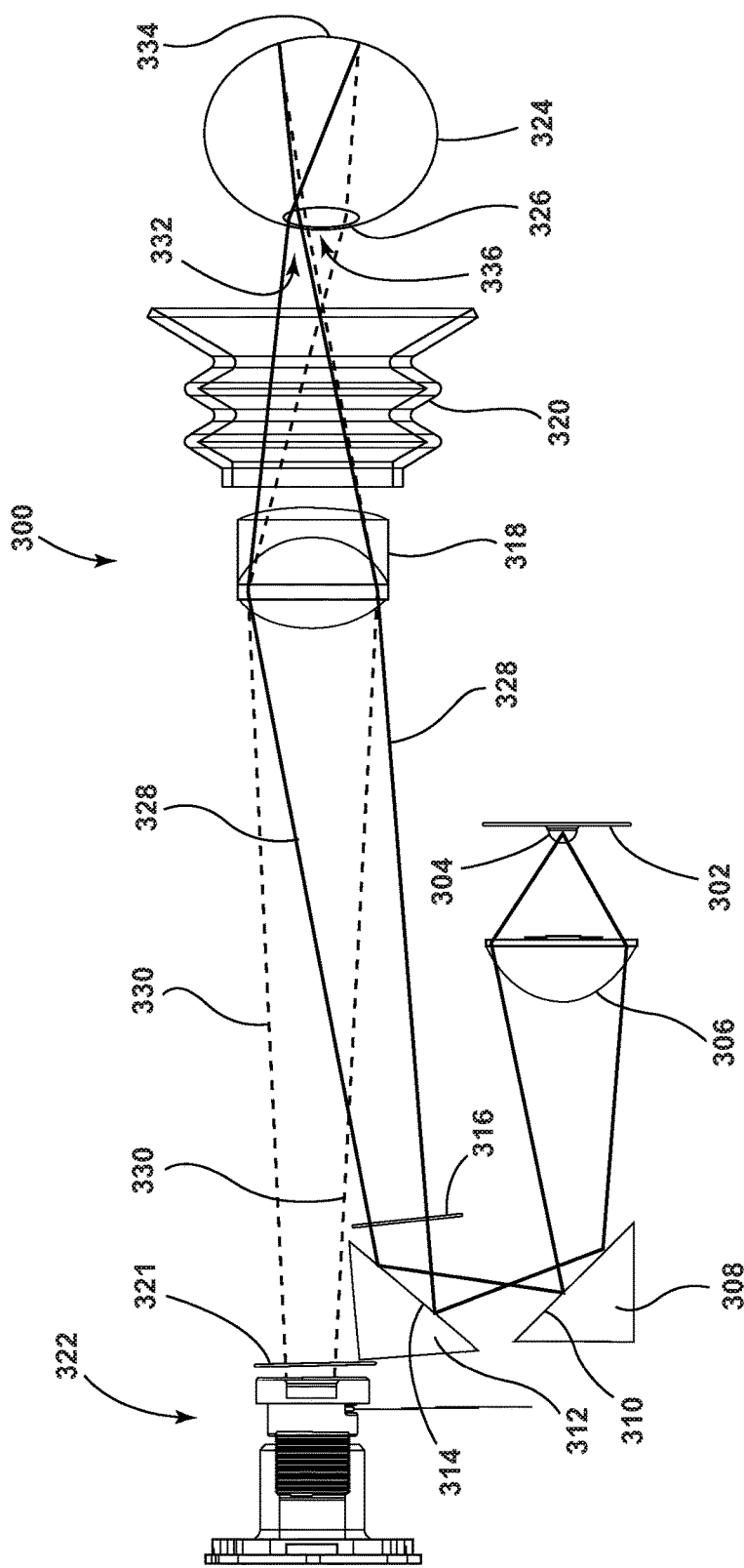
FIG. 13 illustrates an exemplary imaging assembly.

FIG. 13 shows a corresponding system 300 of the above description. System 300 includes an illumination source 302 that includes light source 304. Light source 304, for example, includes both a visible light source and a non-visible light source, and the associated operations may correspond with the above description. That is, light source 304 may include light sources such as light sources 170, 172 as described above. Light source 304 may include a light source that primarily emits visible light such as a light emitting diode (LED), a halogen light source, or an incandescent light source. Exemplary light source 304 may also include a light source that primarily emits non-visible light such as an infrared (IR) light source. That is, if from a non-visible light source, the light emitted therefrom is in a portion of the electromagnetic spectrum that is not visible to a naked eye of a person or the patient. System 300 may include a condensing lens 306 and a first mirror 308 having a first reflective surface 310. A second mirror 312 includes a second reflective surface 314. A first linear polarizer 316 is positioned with a polarization in a first orthogonal orientation. An objective lens 318 is positioned proximate an eye guard 320. A second linear polarizer 321 is positioned proximate a camera assembly 322. Eye 324 includes a pupil opening 326 and a cornea.

In operation and as described above, one or more non-visible light sources may be used to focus the assembly prior to illuminating the eye with visible light to capture an image using camera assembly 322. During the visible light capture of the image, however, reflections off of the objective lens and the cornea can blur or otherwise interfere with a proper capture of the image. Accordingly, the components in system 300 are configured such that the illumination path and the imaging path are decoupled from one another. Referring to system 300, an illumination path 328 is shown as solid lines, and an imaging path 330 is shown as broken lines. Illumination path 328 is emitted from a visible light emitter of light source 304. Emitted light passes from light source 304, such as an LED, through condensing lens 306, and is reflected from first reflective surface 310, to second reflective surface 314, and to objective lens 318. The emitted light passes from objective lens 318 to a first or upper portion 332 of pupil opening 326. The emitted light passes through upper portion 332 to a retina or back surface 334 of eye 324, from which it is reflected or otherwise absorbed and reemitted along imaging path 330. That is, according to the disclosure, light passes from back surface 334 that may be referred to as reflected light, however light may also be absorbed and then emitted from back surface 334, and not necessarily reflected. Or, light emitting from back surface 334 may include a combination of reflected and emitted light. In all such cases, light referred to as either reflected or emitted from back surface 334 is intended, for the purposes of this disclosure, to encompass any light emitted from back surface 334, whether that light be reflected, emitted, or any mechanism in which light emitted therefrom is a result of having light impinging upon back surface 334 along illumination path 328. However, the light from surface 334 passes through a second or lower portion 336 of pupil opening 326. The reflected light passes back to objective lens 318, to second linear polarizer 321, and to camera assembly 322.

According to the disclosure, first linear polarizer 316 places or polarizes light into a first or S orientation, and light reflected off of the objective lens 318 is then rejected by the second linear polarizer 321 that is placed in an orthogonal or P orientation in front of camera assembly 322. The light that passes through objective lens 318 and reaches retina 334 is absorbed and re-emitted in both the P and S orientations, allowing the light that is in the P orientation to pass through second linear polarizer 321 to camera assembly 322. To ensure that there are no corneal reflections, the illumination path and imaging path are decoupled from one another. That is, as shown the illumination path 328 (shown as solid lines) passes through upper portion 332, while the returning light or imaging path 330 (shown as broken lines) passes through lower portion 336. This decoupling means that the light reflected off of the cornea from top portion 332 typically does not find its way back or pass through imaging path 330. Further, although element 332 is described and illustrated as an "upper" portion, and element 336 is described and illustrated as a "lower" portion, it is contemplated that such designations are relative and only for the sake of description. The relevant feature for the purposes of this disclosure is that illumination path 328 passes through one portion of the pupil, and imaging path 330 passes through another portion of the pupil, and the illustrated components are configured to orient and aim the various light paths accordingly and so that the two portions remain separate and decoupled from one another.

Figure 14:
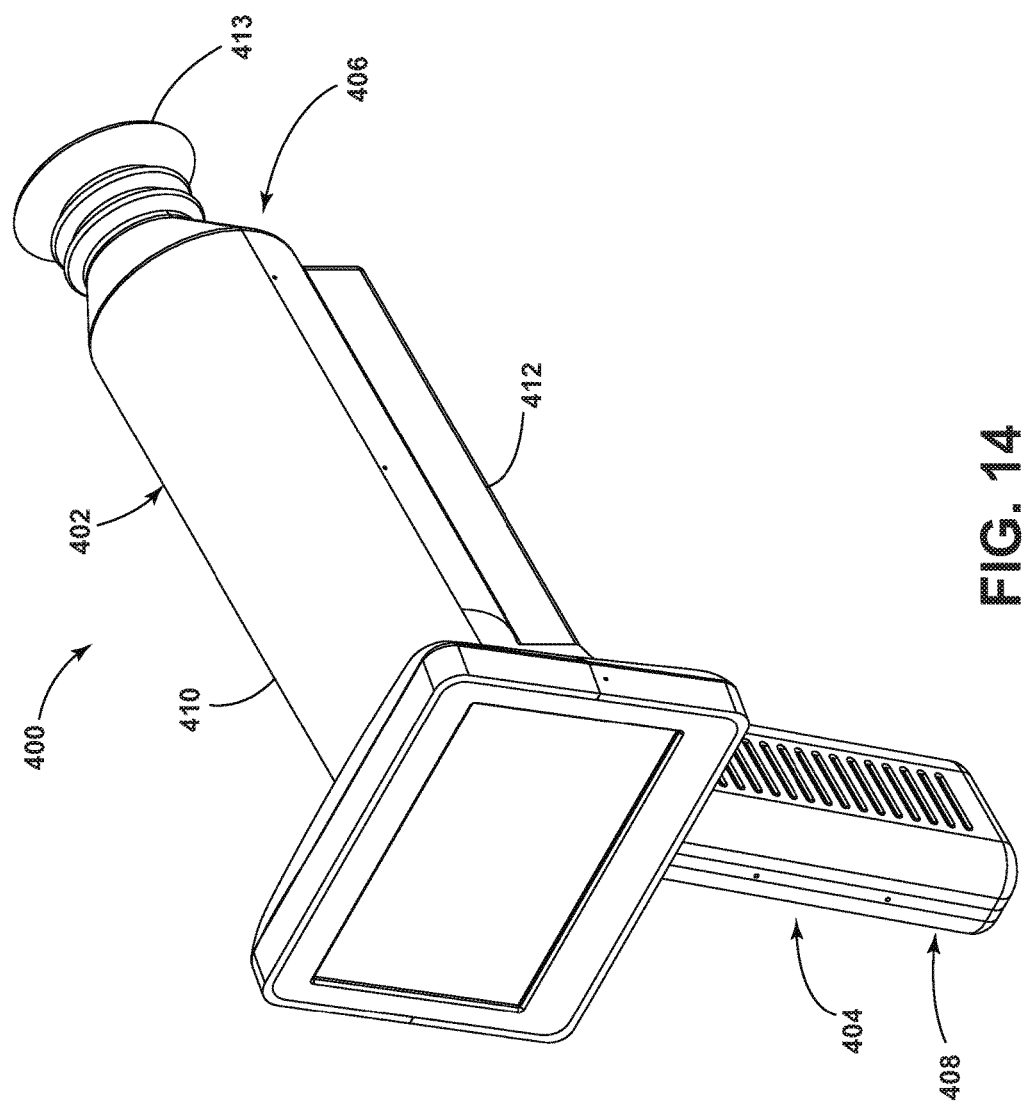
FIG. 14 illustrates an isometric view of an exemplary system of the present disclosure including, for example, the exemplary imaging assembly of FIG. 13.

The present disclosure further includes systems and methods for imaging an eye according to system 300. For instance, FIG. 14 is an isometric, back view of an exemplary system of the present disclosure. FIG. 14 illustrates an exemplary system 400, for example, an ophthalmic system configured to identify eye disorders, which corresponds to system 300 of FIG. 13. System 400 may take many different forms and may include multiple and/or alternate components and facilities. While an exemplary system 400 is shown in FIG. 14, the exemplary components illustrated in FIG. 14 are not intended to be limiting. Indeed, additional or alternative components and/or implementations may be used.

System 400 may be configured to facilitate examination of an eye, for example, to identify, image or photograph, and diagnose an eye disorder by viewing inner structures of the eye including, for example, the retina, optic disc, macula, and posterior pole, also called the fundus. By providing a view of the inner structures of the eye, system 400 may be utilized to diagnose eye disorders.

In an exemplary use, system 400 may be configured to identify an eye disorder, for example, during an eye examination by an examiner or user such as an ophthalmologist, optometrist, optician, eye technician, or any other medical professional. An eye disorder may include, for example, any disorder that is viewable from the inner structures of the eye. Exemplary eye disorders may include any disorder affecting the normal function of the eye, for example, an eye disease, damage to the eye (e.g., resulting from trauma or another bodily disease), or any other vision disorder. Exemplary eye disorders may include, without limitation, diabetic retinopathy, age-related macular degeneration (AMD), allergies, amblyopia (also referred to as "lazy eye"), astigmatism, bacterial keratitis, cataracts, conjunctivitis (also referred to as "pink eye"), detached and torn retina, dry eye, floaters and flashes, glaucoma, low vision, and presbyopia (also referred to as "aging eye"). Accordingly, system 400 may be utilized to identify and diagnose any condition affecting normal function of the eye.

Furthermore, system 400 may be configured to identify other bodily disorders, for example, during a physical examination by a user such as general medical practitioner or any other medical professional. The system may be configured to detect complications viewable from the inner structures of the eye. For example, system 400 may be utilized to identify diabetic retinopathy of the eye resulting from diabetes. System 400 may be utilized to identify hypertension, glaucoma, papilledema, and any other bodily disorder affecting the eye.

As shown in FIG. 14, an exemplary system 400 may include a housing 402. System 400 may include a proximal portion 404 configured for operation by a user and a distal portion 406 configured to be positioned toward and engage an eye socket about an eye of a patient. The housing 402 may include an upper housing portion 410 and a lower housing portion 412, e.g., with the upper housing portion 410 having a lower periphery that engages an upper periphery of the lower housing portion 412.

The housing 402 may include a handle 408, e.g., extending from the lower housing portion 412. The proximal portion 404, the distal portion 406, and the handle 408 may be configured for examination of an eye of a patient by a user. The proximal portion 404 may be configured to be positioned near the user during examination and through which the user examines the eye while holding the handle 408. The distal portion 406 may be configured to be positioned toward the eye during examination. The system 400 may include an engagement member 413 on the distal portion 406 of the housing 402, e.g., having an accordion shape. The engagement member 413 may include proximal portion 404 configured to engage the housing 402 and the distal portion 406 configured to flexibly conform to an eye socket of the patient. A trigger, as described above, may be slidably or rotatably received by the handle 408 and in operative communication with a camera. The trigger may be configured to initiate capture of an image through the engagement member 413, e.g., in response to an inward force by the user and toward the handle 408. The system 400 may be configured to automatically or manually focus and display structures of the eye at multiple depths.

FIGS. 15A, 15B, 15C, 16, 17, 18A, and 18B show Figures having numerical designators corresponding with system 400 of FIG. 13 corresponding to the elements illustrated in FIG. 14. All or any portion of the components herein may be utilized or interchangeable with any of the systems and methods herein.

Figure 15C:
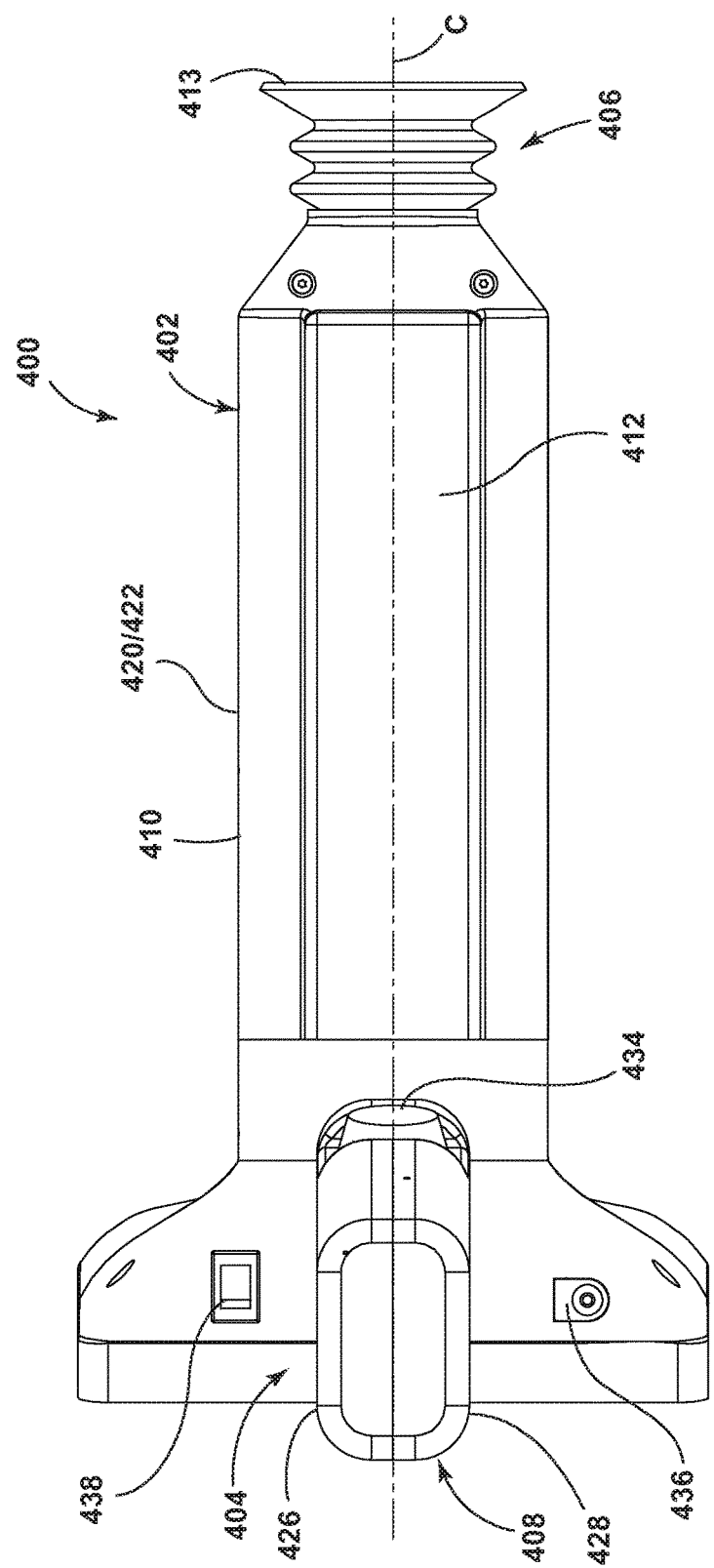
FIG. 15C illustrates a bottom view of the illustration in FIG. 14.

FIG. 15A shows a front perspective view of the illustration in FIG. 14. FIG. 15B shows a side view of the illustration in FIG. 14. FIG. 15C shows a bottom view of the illustration in FIG. 14. As shown in FIG. 15A, a right side handle 426 and a left side handle 428 are combined to form handle 408 of FIG. 14. A faceplate 430 includes a touchscreen display 432. Touchscreen display 432 may include a control panel that may include a plurality of operational buttons or icon-driven features. The control panel may be operatively connected to a lighting assembly and a camera lens assembly, as discussed in further detail below. Buttons may be configured to respectively decrease and increase light intensity of the lighting assembly, and may be configured to change a mode of various modes including a settings mode, an image viewing mode, an image capture mode, and an image transmit mode. Other buttons may be configured to respectively focus out and focus in the camera assembly.

Referring to FIGS. 15B and 15C, a dorsal side housing 420 is attached to a ventral side housing 422. A rubber eye guard 424 includes, for instance, an accordion shape in order that eye guard 424 may be placed proximate an eye of a patient, having flexibility to avoid harm to the patient by pressing too firmly. The housing 420, 422 may various structures that are optimized to engage internal components while facilitating examination of an eye. Housing 420, 422 may include an outer surface that varies in structure from a proximal portion to a distal portion. The housing 420, 422 may further include an inner surface separated a thickness from the outer surface and with the surfaces of the outer surface, but with internal features to engage and secure the internal components. A trigger button 434 may be slidably or rotatably received by the handle 408 and in operative communication with a camera. A charging port 436, such as for charging with DC power or AC power, is positioned and configured to fit a mating charging peg positionable therein. An on-off switch 438 allows for on-off control.

Housing 420, 422 extends along axis C as shown in FIG. 15C. The handle assembly 408 may extend at an angle from a lower portion of the housing 426, 428 may include the trigger button 434 as shown in FIGS. 15B and 15C.

Figure 16:
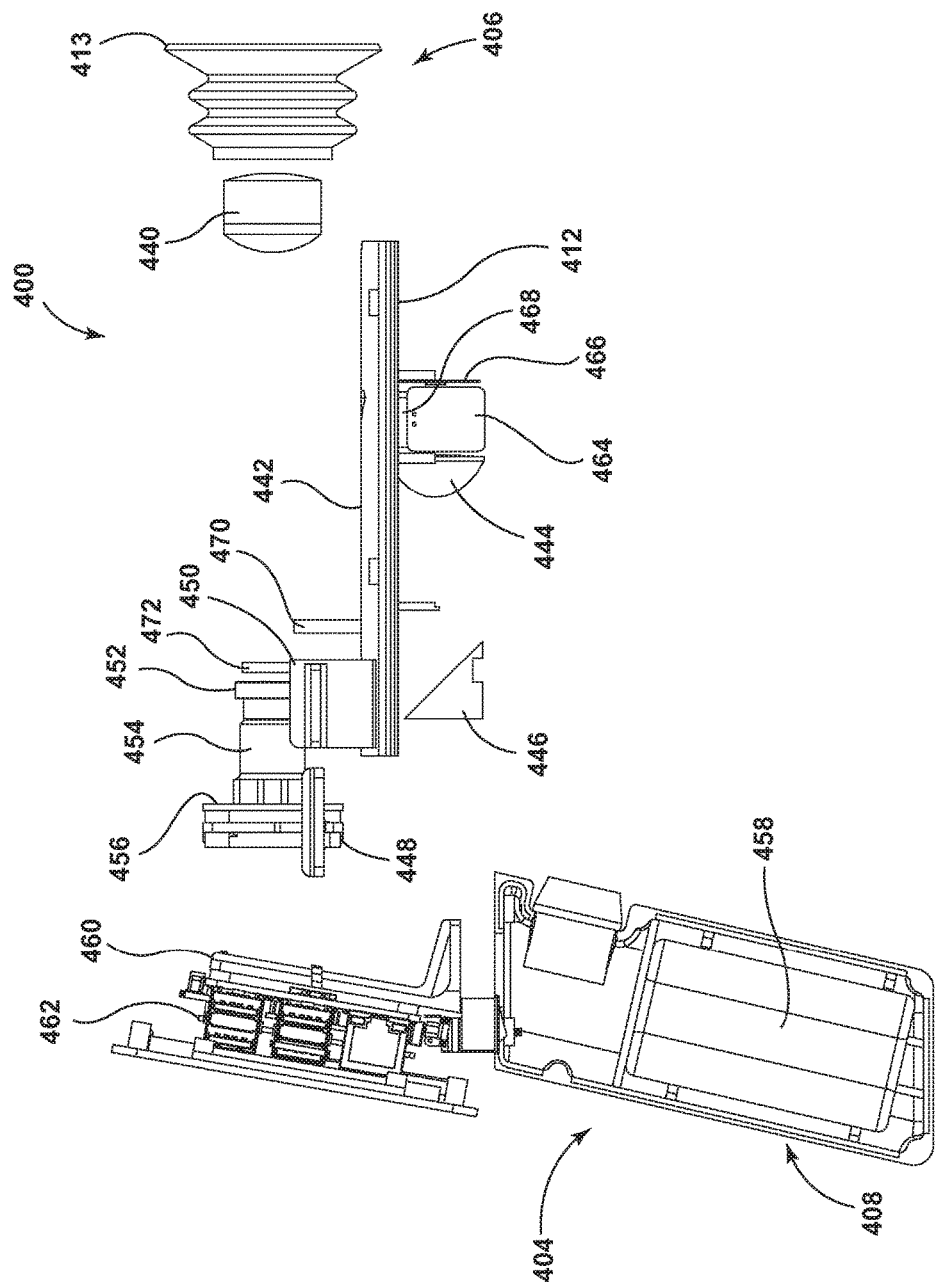
FIG. 16 illustrates an exploded view of exemplary components of the systems herein, for example, as contained in the FIGS. 14, 15A, 15B, and 15C, and including elements described with respect to FIG. 13.

FIG. 16 shows an exploded view including system 400. This may include the components and elements as described with respect to FIGS. 13, 14, 15A, 15B, and 15C.

Objective lens 440 is positioned proximate rubber eye guard 424. An optics cover compartment 442 has attached thereto a beam splitter 468, an infrared (IR) LED module 464 and a visible light LED module 466. Modules 464 and 466 direct their respective outputs to a condensing lens 444, and to a right angle mirror 446. Light passes subsequently to a second right angle mirror within a right angle mirror holder 450. Objective lens 440 corresponds with objective lens 318 of FIG. 13. A focusing lens 452, held by a focusing lens mount 454, is positioned to receive light according to the above description as described with respect to FIG. 13. A camera sensor module 456 thereby is positioned to capture images that correspond also with the description pertaining to FIG. 13, held in place by a camera holder 448. A battery pack 458 is positioned within handle elements 426, 428, and is configured to power operation of all electrical, lens, and other camera components. An electronics assembly mounting bracket 460 includes an electronic assembly 462 that provides all functionality with respect to camera, light, and other operations, to include a controller for interfacing with a user through for instance the touch screen display 432. Some elements described in FIG. 13 may not be illustrated in the exploded view 500, but may be incorporated from the other Figures herein.

Figure 17:
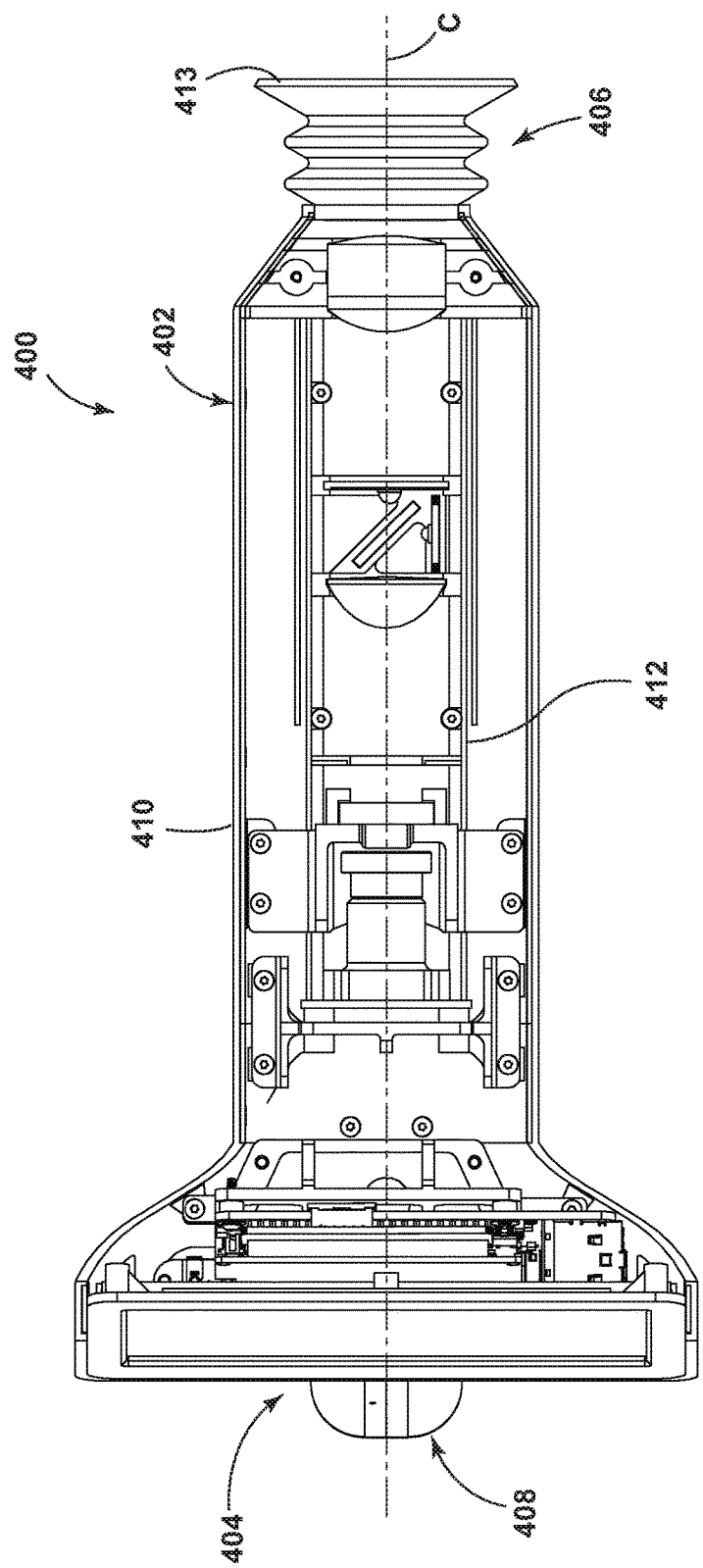
FIG. 17 illustrates a bottom, cutaway view of components contained in the FIGS. 14, 15A, 15B, and 15C.
Figure 18A:
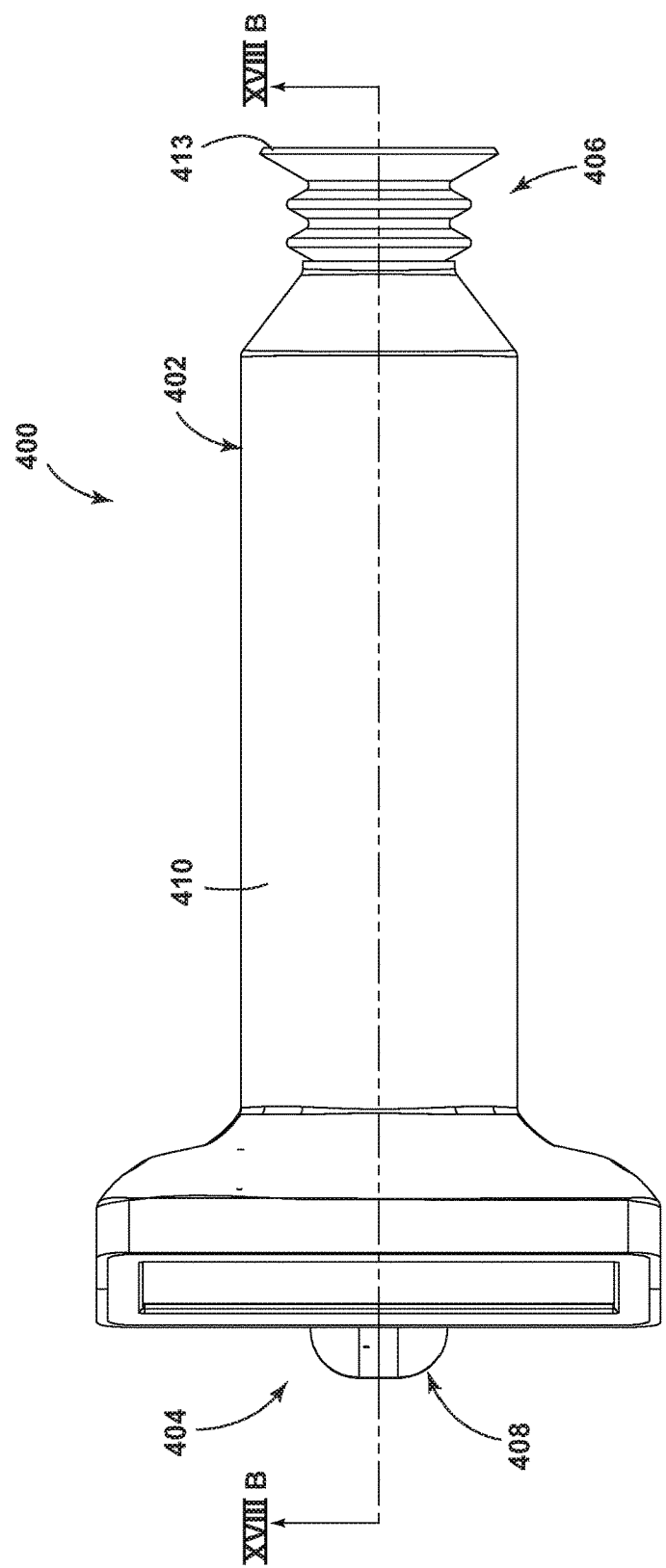
FIG. 18A illustrates a top view of the illustration in FIG. 14.
Figure 18B:
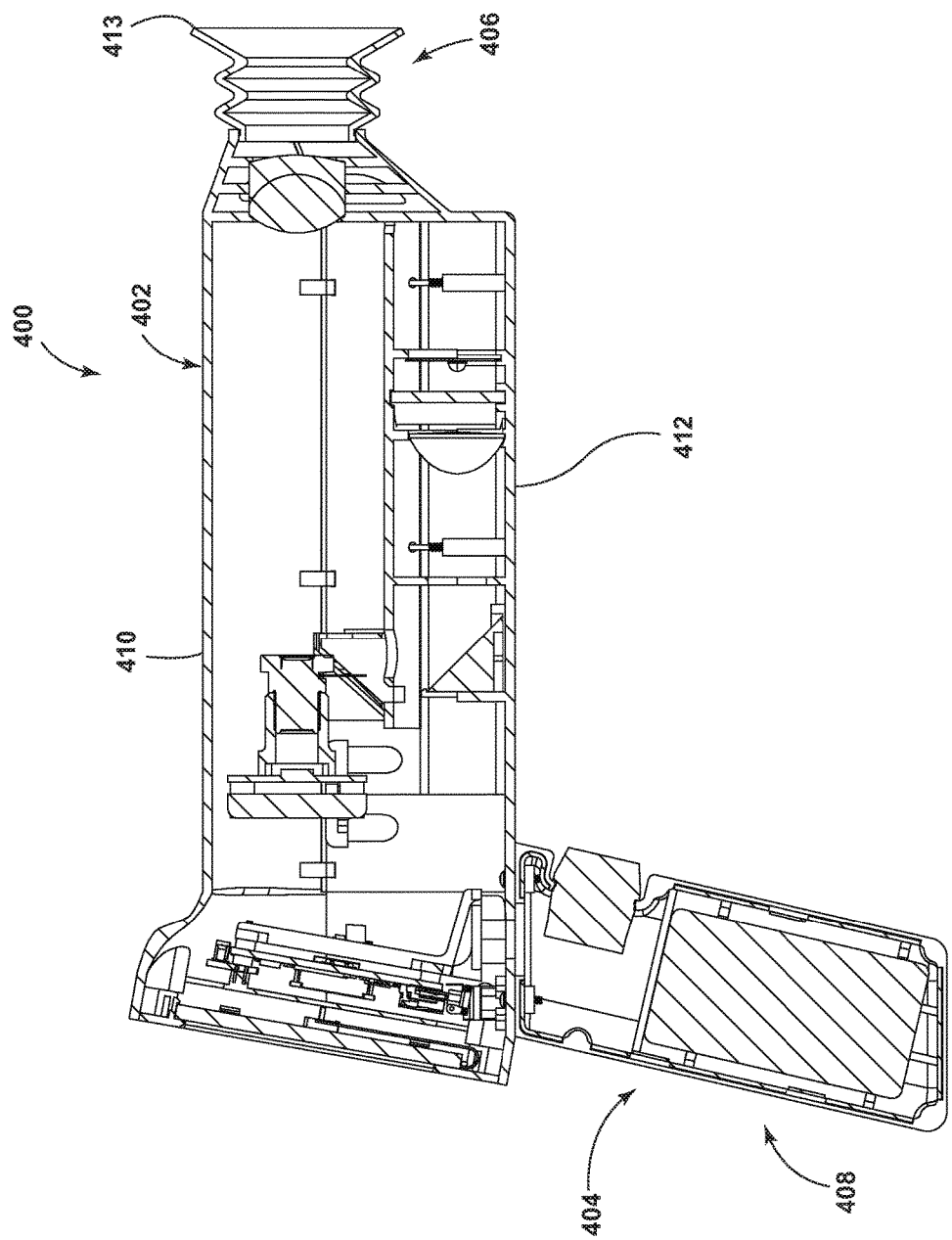
FIG. 18B illustrates a side view of the illustration in FIG. 14.

FIG. 17 is a bottom view of components contained in the FIGS. 14, 15A, 15B, and 15C, having components illustrated and corresponding to FIGS. 14-16. Likewise, FIG. 18A is a top view of the illustration in FIG. 14, and FIG. 18B is a side view of the illustration in FIG. 14.

FIGS. 14-18B illustrate components that correspond with system 400 of the above description, and corresponding with the description as it pertains to FIG. 13. System 400 also incorporates the features described with respect to FIGS. 1-13 above, as well. System 400 includes an illumination source that includes both visible light source 466 and non-visible light source 464, and the associated operations may correspond with the above description. That is, light sources 464, 466 may include light sources such as light sources 170, 172 as described above. Light source 466 may include a light source that primarily emits visible light such as a light emitting diode (LED), a halogen light source, or an incandescent light source. Exemplary light source 464 may also include a light source that primarily emits non-visible light such as an infrared (IR) light source. System 400 may include condensing lens 444 and mirror 446 having a first reflective surface. Mirror 450 includes a second reflective surface. A first linear polarizer 470 is positioned with a polarization in a first orthogonal orientation. A second linear polarizer 472 is positioned proximate a camera sensor module 456.

In operation and as described above, one or more non-visible light sources may be used to focus the assembly prior to illuminating the eye with visible light to capture an image using camera assembly 456. During the visible light capture of the image, however, reflections off of the objective lens and the cornea can blur or otherwise interfere with a proper capture of the image. Accordingly, the components in system 400 are configured such that the illumination path and the imaging path are decoupled from one another, as described above with respect to system 300 of FIG. 13. Thus, components described above in system 400 correspond with the illustrated discussion of system 300 of FIG. 13.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An ophthalmic system for imaging an eye, the system comprising:
   an eye guard positionable proximate an eye of a patient;
   an objective lens generally aligned with the eye guard, such that light passes through the objective lens in a first direction along an illumination path that passes through the eye guard;
   a light source positioned to emit imaging light toward the objective lens in the first direction along the illumination path;
   a first mirror positioned to receive and reflect the imaging light from the light source;
   a second mirror positioned to receive and reflect the reflected light from the first mirror; and
   a camera assembly positioned to receive emitted light that is emitted from a back surface of the eye, the emitted light passing along an imaging path that passes through the objective lens and in a second direction that is opposite the first direction,
   wherein the light source and the objective lens are positioned such that, when the eye guard is positioned proximate the eye of the patient, the light from imaging light passes through a first portion of a pupil opening in the eye, and the emitted light passes through a second portion of the pupil opening of the eye that is different from the first portion, wherein the reflected light from the second mirror passes to the objective lens as the imaging light that is emitted toward the objective lens, and wherein the camera assembly captures an image of the eye using the emitted light.

2. The system of claim 1, wherein the light source is a non-visible light source that emits imaging light is in a non-visible portion of the electromagnetic spectrum.

3. The system of claim 1, further comprising a first linear polarizer positioned between the second mirror and the objective lens, the first linear polarizer positioned to have a first plane of polarization.

4. The system of claim 3, further comprising a second linear polarizer positioned between the objective lens and the camera assembly, the second linear polarizer positioned to have a second plane of polarization that is different from the first plane of polarization.

5. The system of claim 1, wherein the camera assembly and the objective lens are arranged in an optical path that is substantially free of mirrored surfaces from the objective lens to the camera assembly.

6. The system of claim 1, further comprising a housing that includes an upper housing portion, a lower housing portion, and a handle, the upper and lower housing portions opposingly engaging each other, the handle extending from the lower housing portion, and the handle including a trigger configured to be received therein.

7. The system of claim 1, further comprising a control assembly and a display communicatively connected to the control assembly and configured to display the image of the eye.

8. The system of claim 1, further comprising a controller configured to focus the camera assembly using the light source, which is one of a visible light source and a non-visible light source.

9. A method of using an ophthalmic system for imaging an eye of a patient, the method comprising:
   positioning an eye guard proximate an eye of a patient;
   aligning an objective lens with the eye guard, such that light passes through the objective lens in a first direction along an illumination path that passes through the eye guard;
   positioning a light source to emit imaging light toward the objective lens in the first direction along the illumination path;
   providing a first mirror to receive and reflect the imaging light from the light source;
   providing a second mirror to receive and reflect the reflected light from the first mirror;
   positioning a camera assembly to receive emitted light that is emitted from a back surface of the eye, the emitted light passing along an imaging path that passes through the objective lens and in a second direction that is opposite the first direction; and
   capturing an image of the eye using the emitted light,
   wherein the light source and the objective lens are positioned such that, when the eye guard is positioned proximate the eye of the patient, the light from imaging light passes through a first portion of a pupil opening in the eye, and the emitted light passes through a second portion of the pupil opening of the eye that is different from the first portion, and wherein the reflected light from the second mirror passes to the objective lens as the imaging light that is emitted toward the objective lens.

10. The method of claim 9, wherein positioning the light source comprises positioning a non-visible light source that emits imaging light is in a non-visible portion of the electromagnetic spectrum.

11. The method of claim 9, further comprising positioning a first linear polarizer between the second mirror and the objective lens, the first linear polarizer positioned to have a first plane of polarization.

12. The method of claim 11, further comprising positioning a second linear polarizer between the objective lens and the camera assembly, the second linear polarizer positioned to have a second plane of polarization that is different from the first plane of polarization.

13. The method of claim 9, further comprising arranging the camera assembly and the objective lens in an optical path that is substantially free of mirrored surfaces from the objective lens to the camera assembly.

14. The method of claim 9, further comprising providing a housing that includes an upper housing portion, a lower housing portion, and a handle, the upper and lower housing portions opposingly engaging each other, the handle extending from the lower housing portion, and the handle including a trigger configured to be received therein.

15. The method of claim 9, further comprising providing a control assembly and a display communicatively connected to the control assembly to display the image of the eye.

16. The method of claim 9, further comprising providing a control assembly that includes memory to store the image of the eye.

17. An ophthalmic system for imaging an eye, the system comprising:
   an eye guard;
   an objective lens generally aligned with the eye guard, such that visible imaging light passes through the objective lens along an illumination path that passes through the eye guard;
   a light source positioned to emit the visible imaging light toward the objective lens along the illumination path;
   a first mirror positioned to receive and reflect the imaging light from the light source;
   a second mirror positioned to receive and reflect the reflected light from the first mirror; and
   a camera assembly positioned to receive emitted light that is emitted from a back surface of the eye, the emitted light passing along an imaging path that passes through the objective lens;
   wherein the light source and the objective lens are positioned such that, when the eye guard is positioned proximate the eye of the patient, the imaging light passes through a first portion of a pupil opening in the eye, and the emitted light passes through a second portion of the pupil of the eye that is different from the first portion, wherein the reflected light from the second mirror passes to the objective lens as the imaging light that is emitted toward the objective lens, and wherein the camera assembly captures an image of the eye using the emitted light.

18. The system of claim 17, further comprising:
   a first linear polarizer positioned between the second mirror and the objective lens, the first linear polarizer positioned to have a first plane of polarization; and
   a second linear polarizer positioned between the objective lens and the camera assembly, the second linear polarizer positioned to have a second plane of polarization that is different from the first plane of polarization.

19. The system of claim 17, wherein the camera assembly and the objective lens are arranged in an optical path that is substantially free of mirrored surfaces from the objective lens to the camera assembly.

20. The system of claim 17, further comprising a housing that includes an upper housing portion, a lower housing portion, and a handle, the upper and lower housing portions opposingly engaging each other, the handle extending from the lower housing portion, and the handle including a trigger configured to be received therein.

* * * * *